US006439054B1

(12) United States Patent
Gore et al.

(10) Patent No.: US 6,439,054 B1
(45) Date of Patent: Aug. 27, 2002

(54) METHODS OF TESTING SPUTTERING TARGET MATERIALS

(75) Inventors: Russell B. Gore; Ronald H. Fleming, both of Spokane, WA (US)

(73) Assignee: Honeywell International Inc., Morristown, NJ (US)

( * ) Notice: Subject to any disclaimer, the term of this patent is extended or adjusted under 35 U.S.C. 154(b) by 63 days.

(21) Appl. No.: 09/585,242

(22) Filed: May 31, 2000

(51) Int. Cl.$^7$ .............................................. G01N 29/04
(52) U.S. Cl. .............................. 73/620; 73/623; 73/602
(58) Field of Search ..................... 73/620, 630, 599, 73/159, 615, 618, 588, 600, 625, 626, 627, 628, 641, 637, 622, 642, 597, 598, 601, 602

(56) References Cited

U.S. PATENT DOCUMENTS

| | | | | |
|---|---|---|---|---|
| 4,056,971 A | * | 11/1977 | Van Valkenburg et al. | ... 73/629 |
| 4,441,369 A | * | 4/1984 | Lessard et al. | ................ 73/628 |
| 4,467,653 A | * | 8/1984 | Turbe | .......................... 73/620 |
| 4,475,394 A | * | 10/1984 | Takeda et al. | ................. 73/660 |
| 4,893,510 A | * | 1/1990 | Ichikawa et al. | .............. 73/620 |
| 4,914,952 A | * | 4/1990 | Miyajima et al. | ............. 73/600 |
| 5,125,514 A | * | 6/1992 | Oehler et al. | ................... 73/627 |
| 5,406,850 A | * | 4/1995 | Bouchard et al. | ............. 73/620 |
| 5,887,481 A | | 3/1999 | Leroy et al. | .................... 73/627 |
| 5,955,673 A | * | 9/1999 | Leroy et al. | .................... 73/602 |
| 6,269,699 B1 | * | 8/2001 | Gilman et al. | ................. 73/601 |

FOREIGN PATENT DOCUMENTS

| | | |
|---|---|---|
| EP | 0 583 136 A1 | 7/1998 |
| FR | 2 800 467 A1 | 5/2001 |
| GB | 2 019 566 A | 10/1979 |
| GB | 2 167 860 A | 6/1986 |
| WO | WO 98/24945 | 6/1998 |
| WO | WO 99/64854 | 12/1999 |

OTHER PUBLICATIONS

"Correlation between Aluminum Alloy Sputtering Target Metallurgical Characteristics, Arc Initiation, and In–Film Defect Density" by Vikram Pavate et al. SPIE vol. 3214 p. 42–47.

* cited by examiner

Primary Examiner—Helen Kwok
(74) Attorney, Agent, or Firm—Wells St. John P.S.

(57) ABSTRACT

The invention includes a method for testing materials, such as for example sputtering target materials, other materials for electronics applications, or other materials in general in which homogeneity throughout the material is desired. A plurality of positions are defined across at least a portion of a material. Sonic energy is sequentially irradiated across the plurality of positions. Echoes are induced by the sonic energy, and detected. At least some of the detected echoes are associated with individual positions of the plurality of positions that triggered the detected echoes. Information pertaining to at least one physical attribute of the detected echoes is processed to sort the detected echoes into a first group indicative of inhomogeneities in the material, and a second group which does not indicate inhomogeneities in the material. The echoes of the first group are sorted into clusters, with the clusters being defined as echoes from adjacent positions of the plurality of positions. The separate echoes associated with a common cluster are analyzed and considered together to generate information about an inhomogeneity in the material.

47 Claims, 8 Drawing Sheets

METHODS OF TESTING SPUTTERING TARGET MATERIALS

TECHNICAL FIELD

This invention pertains to methods of testing materials, including methods of testing sputtering target materials. The sputtering target materials can be tested before the materials have acquired a sputtering target form (for instance, as-cast materials), and methods of testing the materials after they have acquired a sputtering target form (with sputtering target form referring to microscopic features, such as, for example, grain size and orientation), including methods of testing the materials after they have been processed into a sputtering target shape. In particular applications, the invention pertains to non-destructive evaluation of sputtering target materials through the use of ultrasonic testing technologies.

BACKGROUND OF THE INVENTION

One method of applying thin films of materials during manufacturing of integrated electronic circuits is sputtering of the materials from a target. The sputtering comprises forming a target of a material which is to be deposited, and providing the target as a negatively charged cathode proximate a strong electric field. The electric field is utilized to ionize a low pressure inert gas and thereby form a plasma. Positively charged ions in the plasma are accelerated by the electric field toward the negatively charged cathode (i.e., toward the sputtering target). The ions impact the sputtering target, and thereby eject target material. The ejected target material is primarily in the form of atoms or groups of atoms, and can be utilized to deposit thin, uniform films on substrates placed in the vicinity of the target during the sputtering.

It is frequently desired to manufacture sputtering targets to tight tolerances to ensure uniformity in the thickness and conformity of layers formed by sputtering materials from the targets. A problem that can occur during the manufacture of sputtering targets is formation of discontinuities (i.e. heterogeneous regions) in sputter target material. Exemplary discontinuities are voids, cracks and changes in porosity throughout a material, as well as solid inclusions. The sputter target discontinuities can lead to unipolar arcing during a sputtering process. Unipolar arcing can cause localized overheating and explosion of target material, and can thus decrease the uniformity and conformity of thin film deposition on a substrate. Additionally, if the discontinuities are inclusions or other regions comprising impurities, sputtering from the discontinuities can result in particles of the discontinuities being deposited onto a substrate.

As integrated circuit devices become increasingly smaller, tolerances for uniformity, conformity and undesired particles decrease. Accordingly, it is desired to form better (i.e. more homogeneous) target materials, and also desired to develop testing technologies which can distinguish homogeneous target materials from inhomogeneous target materials.

Among the techniques which can be most useful for testing target materials are techniques which are non-destructive to the materials. In other words, techniques which evaluate the materials but which still enable the materials to be utilized in formation and utilization as sputtering targets. A non-destructive technique which has received recent interest is ultrasonic testing. For instance, ultrasonic testing technologies are described in PCT International Application Number PCT/US99/13066 and U.S. Pat. No. 5,887,481. General principles of ultrasonic testing technology are also described in a Non-Destructive Testing Handbook (A. S. Birks, R. E. Green, P. McIntire, *Non-Destructive Testing Handbook, Ultrasonic Testing*, Second Edition, Vol. 7, American Society for Non-Destructive Testing, 1991.)

Figure 1:
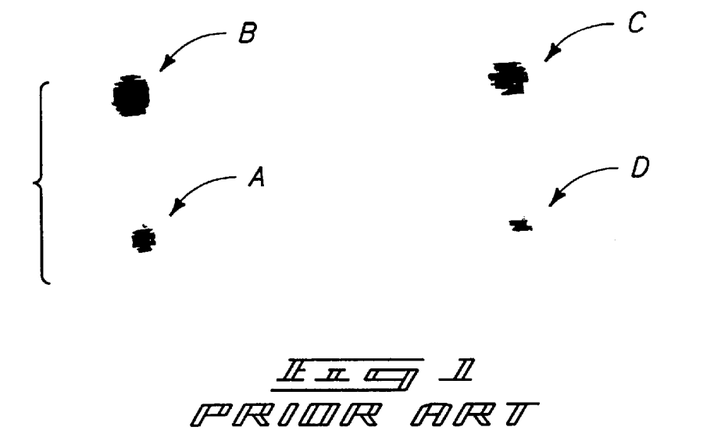
FIG. 1 is a C-scan image of flat bottom holes in a sputtering target material, with the imaging of the flat bottom holes being conducted in accordance with prior art C-scanning methodologies.

The Non-Destructive Testing Handbook describes modem C-scan ultrasonic testing equipment. Such equipment uses an automated X-Y raster scan of an ultrasonic transducer relative to a tested material. The transducer scans parallel, and in close proximity to a surface of the sample, with the sample and transducer both being coupled through a sound conducting medium, such as, for example, water, oil, or a gel. At each point in the scan, a pulse of ultrasound is transmitted from the ultrasonic transducer, through the sound-conducting medium, and into the sample. The pulse travels from the transducer as an "ultrasonic beam". A fraction of the ultrasonic beam can be reflected, refracted or scattered back to the transducer from discontinuities in the path of the beam. The ultrasound signals returned to the transducer are converted into electrical signals. The electrical signals are processed so that only signals returned from discontinuities located within a specified depth range below the sample surface are evaluated. For each point in the raster scan, the amplitude and time is recorded for the largest amplitude signal that corresponds with the specified depth range. The amplitude and time data for all scan points comprise a so-called findamental data set. The amplitude data are often coded by color or shade and plotted versus scan position in a "C-scan image," such as, for example, the image shown in FIG. 1. The image of FIG. 1 shows four "defects" (actually flat-bottom holes) in a target material, with the defects labeled as "A", "B", "C" and "D".

Compensation for various depth effects can be achieved by applying a multiplicative correction factor to the C-scan amplitude. The depth correction can be applied during analog signal processing (for example, utilizing a time varied gain), or during digital processing, (for example, utilizing depth amplitude correction). The depth correction factor can be derived from measurements of flat bottom holes of a specified diameter. The flat bottom holes are drilled various depths into the back surface of a standard, which is measured using ultrasound incident on the front surface. The front and back surfaces of the standard are parallel, and the holes are normal to these surfaces. The distance from the front surface to the blind-end of a flat bottom hole is considered the depth of the flat bottom hole with respect to ultrasound testing. Depth amplitude correction factors are derived for depths corresponding to the available flat bottom hole depths, and interpolated or extrapolated for other depths. The size of an unknown defect can be estimated by comparison to flat bottom hole reference standards.

U.S. Pat. No. 5,887,481 and PCT Application Number PCT/US99/13066 describe particular applications of ultrasound testing technology to the testing of target materials. For instance, U.S. Pat. No. 5,887,481 describes a method of sorting aluminum target materials into several grades based on the number of defects per cubic centimeter detected by ultrasonic testing technology. One potential drawback of U.S. Pat. No. 5,887,481 is that the estimation of a defect size is generally based on only a single (highest amplitude) datapoint. Depending on the relative position of the defect and the raster scan points, differences in maximum amplitude are expected. PCT Application No. PCT/US99/13066 discusses U.S. Pat. No. 5,887,481 in detail, and provides techniques to overcome perceived shortcomings in U.S. Pat. No. 5,887,481. For instance, PCT/US99/13066 describes a method which avoids the units of defect per cubic centimeter, and rather presents defect information as a histogram. Instead of estimating the size of individual defects, PCT/US99/13066 analyzes the amplitude distribution of all datapoints in a C-scan ultrasonic testing type analysis. Any datapoint in the analysis having an amplitude which exceeds a threshold is considered a defect datapoint. The threshold is determined based on measurements of flat bottom hole reference standards and target material samples. A so-called "cleanliness" factor is calculated as a ratio of defect datapoints (referred to in PCT/US99/13066 as "flaw datapoints") to total datapoints. Alternatively, a histogram may be generated by counting the number of datapoints which fall into various "amplitude bands."

While U.S. Pat. No. 5,887,481 and PCT/US99/13066 present advances in methods for analyzing target materials, there are difficulties associated with the techniques. It would be desirable to develop improved techniques for utilizing ultrasound in determining homogeneity of target materials.

SUMMARY OF THE INVENTION

In one aspect, the invention encompasses a method for testing materials, such as for example sputtering target materials, other materials for electronics applications, or other materials in general in which homogeneity throughout the material is desired. A plurality of positions are defined across at least a portion of a material. Sonic energy is sequentially irradiated across the plurality of positions. Echoes are induced by the sonic energy, and detected. At least some of the detected echoes are associated with individual positions of the plurality of positions that triggered the detected echoes. Information pertaining to at least one physical attribute of the detected echoes is processed to sort the detected echoes into a first group indicative of inhomogeneities in the material, and a second group which does not indicate inhomogeneities in the material. The echoes of the first group are sorted into clusters, with the clusters being defined as echoes from adjacent positions of the plurality of positions. The separate echoes associated with a common cluster are analyzed and considered together to generate information about an inhomogeneity in the material.

BRIEF DESCRIPTION OF THE DRAWINGS

Preferred embodiments of the invention are described below with reference to the following accompanying drawings.

FIG. 9 shows that angled beam ultrasound, alone or in combination with normal incidence ultrasound, can be useful in distinguishing solid-inclusion-type defects from flattened-void-type defects.

DETAILED DESCRIPTION OF THE PREFERRED EMBODIMENTS

The invention encompasses methods for testing sputtering target materials utilizing sonic energy, such as, for example, ultrasound energy. For purposes of interpreting this disclosure and the claims that follow, a sputtering target material is to be understood as a material suitable for formation of a sputtering target. The material can be in the form of a sputtering target, or can be in a different form. For example, the material can be in the form of a billet, which would be subsequently rolled and otherwise shaped into a sputtering target configuration. For purposes of interpreting this disclosure and the claims that follow, it is to be understood that a material is in a sputtering target "form" when it has a grain size and texture suitable for utilization as a sputtering target, and that the material can have such form before it is processed to have the final shape of a sputtering target.

Exemplary sputtering target materials comprise metal, consist essentially of metal, or consist of metal; and can comprise, for example, one or more of aluminum, copper, titanium, tungsten, tantalum, gold, and alloys thereof. Some particular target materials that can be utilized in methods of the present invention are materials that consist essentially of one or more of aluminum, copper and silicon. In addition to the metallic constituents, the materials can also comprise small amounts of impurities, such as, for example, silicon dioxide, aluminum oxide, carbon, hydrogen and/or air. The impurities can be in the form of inclusions (solid or gaseous) within the metallic materials of the target. Such inclusions represent one type of inhomogeneity which can be present in a target material.

It is to be understood that the above-described sputtering target materials are exemplary target materials, and that other target materials can be utilized in methodology of the present invention. For instance, methodology of the present invention can be utilized for testing nonmetallic target materials, such as, for example, ceramic materials.

The background section of this disclosure indicated that ultrasonic testing of target materials is known in the art, and further indicated that PCT/US99/13066 and U.S. Pat. No. 5,887,481 describe exemplary methods for utilizing ultrasonic testing relative to sputtering materials. The background section also indicated that difficulties exist with the present methods, but did not elaborate on the difficulties. A few particular difficulties are described herein to assist in explaining certain advantages of the present invention relative to prior art methods.

One of the difficulties that can occur in utilizing prior art methods is in compensating for different levels of ultrasonic transducer performance. Ultrasonic transducers can have different levels of performance due to degradation of transducers during the lifetime of the transducers, and further due to differences which exist between individual transducers as manufactured. Prior art methods do not typically discern and compensate for differences between transducers.

Another difficulty with prior art methods is that the methods do not attempt to categorize information relative to particular inhomogeneities (with the term "inhomogeneity" being defined to encompass at least some of the defects with can occur within a sputtering target material). For instance, U.S. Pat. No. 5,887,481 effectively utilizes information from only a highest amplitude point of a given defect for analyzing the defect. PCT/US99/13066 ascertains and analyzes data from multiple C-Scan points across a target, but does not attempt to combine data obtained from the same defect in a target material. Also, although it is recognized that defects can take the form of either voids or solid inclusions, prior art methods do not generally attempt to categorize defects amongst the two broad classes of inclusions and voids, and do not take into consideration the differences in ultrasonic response to the different kinds of defects.

Another difficulty with prior art techniques of ultrasonic analysis of target materials is that depth effects are not fully accounted for. In typical methods, the same depth correction factor is applied to defects of all sizes. In considering the complex geometry of a focused ultrasound beam, however, there is no reason to expect that the depth correction should be independent of defect size. Uncertainties in depth correction can further compound uncertainties caused by analyses which utilize only one point per defect, or which ignore information contained in the grouping of datapoints.

Another difficulty in prior art methods of utilizing ultrasound methods for analyzing target materials is that non-uniform erosion of sputter targets is typically not addressed. Instead, it is typically assumed that results obtained within a constant depth range of a material will represent the material within the non-uniform erosion profile. However, in many cases such is a bad assumption.

The present invention provides technologies which can improve ultrasonic testing of sputtering target materials and overcome one or more of the above-discussed difficulties. Also, although the invention is described for utilization in testing target materials, it is to be understood that the invention can also be utilized for general testing of substantially homogeneous materials for inhomogeneities within the materials, such as, for example, for testing solders. In the context of this document a "substantially homogeneous" material is to be understood as a material which is more than 95% homogeneous.

The present invention utilizes an analysis threshold to distinguish between background and defect signals. The threshold is generally kept higher than a background signal, but close enough to the background signal to avoid excessive rejection of defect signals. The background signal can be determined as the range of signal amplitude measured for sections of material having no defects discernible in an ultrasonic C-scan image analysis. Alternatively, the threshold can be lowered to the level where only a small fraction of datapoints exceed the threshold, and then a minimum cluster area can be used to eliminate the isolated datapoints where the background signal exceeds the threshold.

A method of the present invention comprises a C-scan across a surface of a target material. An exemplary process is described diagrammatically with reference to a system 100 in FIG. 2. A sputtering target material 10 is placed within a vessel 12 having a liquid 14 therein. Liquid 14 can comprise, for example, distilled water. Sputtering target material 10 can be 20 supported by a support structure (not shown) to hold material 10 off of a bottom of vessel 12. Material 10 is shown as a mass in the form of a processed sputtering target material, and is shown to comprise a top surface 16 and a bottom surface 18 parallel to top surface 16. It is to be understood that the shape of material 10 is exemplary, and material 10 could comprise other shapes, such as, for example, an ingot which has not yet been compressed into a target shape.

Figure 2:
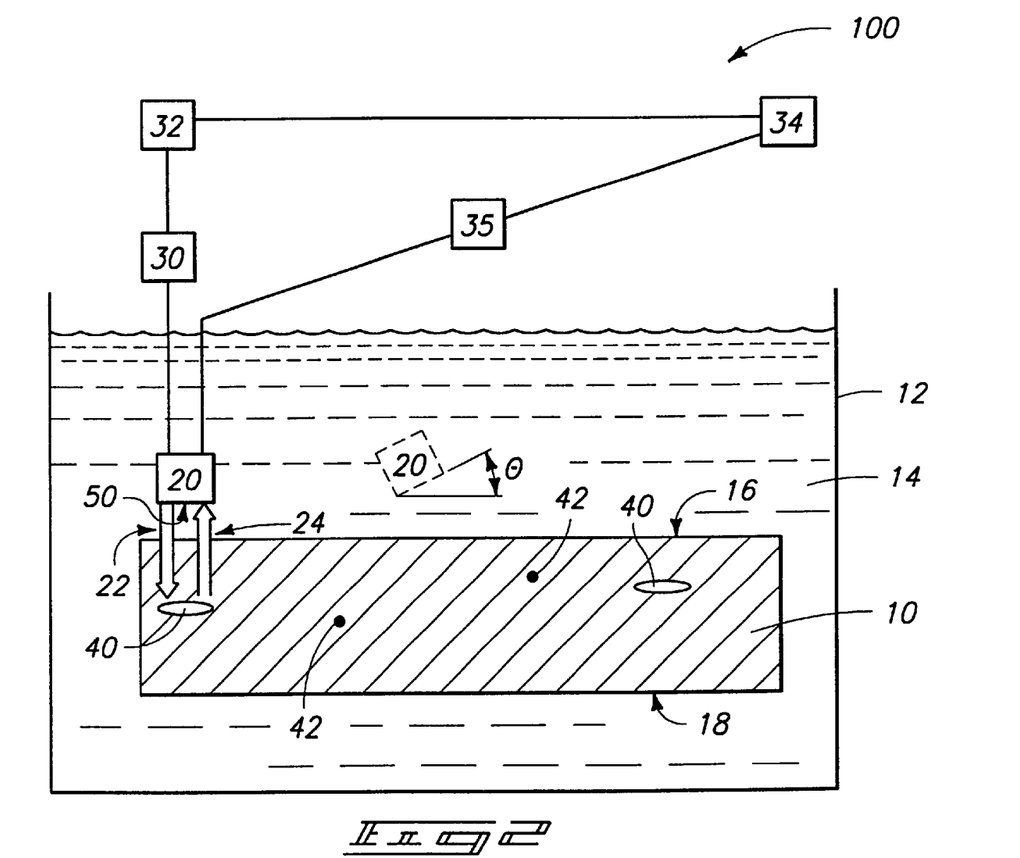
FIG. 2 is a diagrammatic view of a system suitable for a method of the present invention, with a portion of the system shown in cross-sectional side view.

A transducer 20 is positioned within liquid 14 and above surface 16 of material 10. Transducer 20 is defined to be "directly" over a portion of surface 16 that is immediately below transducer 20, and not "directly" over other portions of surface 16, but instead is simply above such other portions.

Transducer 20 can be provided to be spaced by a distance of, for example, about ½ inch above surface 16. Transducer 20 irradiates upper surface 16 with an ultrasonic pulse 22. Subsequently, transducer 20 detects an echo 24 reflected back from a feature (inhomogeneity) 40 within material 16. Transducer 20 converts the echo into an electrical signal which is processed for use in characterizing material 10. Specifically, the amplitude of echo 24, as well as the time between input of pulse 22 and receipt of echo 24, can be used in determining if defects are present within material 10. Material 10 is shown to have a substantially planar and smooth upper surface 16, and such can be a preferred property of material 10 to alleviate multidirectional scattering of ultrasound by surface 16. Surface 16 can, for example, have a surface characterized by less than 50 micro-inches of roughness. It is noted that although upper surface 16 is shown to be a flat expanse, the surface can alternatively be curved, and could, for example, comprise a cylindrical outer surface of an ingot. In circumstances in which surface 16 is a cylindrical outer surface of an ingot, the ingot can be rotated to accomplish the Y-direction scanning across the surface, the transducer or ingot can be moved to accomplish the X-direction scanning.

Transducer 20 is shown mounted on a mechanical X-Y C-scanner 30 which is in electrical communication with a controller 32. Controller 32 is in data communication with a processor 34. Processor 34 is also in data communication with a pulser/receiver 35 that is coupled to transducer 20.

Controller 32 can be programmed to induce mechanical X-Y scanning unit 30 to move transducer 20 in a raster-like stepwise motion across upper surface 16 of material 10. Accordingly, a plurality of positions are defined across at least a portion of upper surface 16. Transducer 20 is moved sequentially to each of the positions where it is triggered by pulser/receiver 35 to irradiate material 10 with sonic energy.

A suitable transducer and processing system for utilization in methods of the present invention is the Panametrics Multiscan™ system utilizing a 9100™ signal generator/processor (pulser-receiver), and also utilizing ScanView™ software with clustering utility including depth and average amplitude report. An exemplary transducer is a Panametrics V317SU™.

A preferred frequency of sonic radiation 22 generated by transducer 20 is within the range of from 5 MHz to 100 MHz, with a more preferred frequency being from about 5

MHz to about 25 MHz, and a typical frequency being within the range of from 10 MHz to 20 MHz.

Preferably, adjacent data acquisitions steps defined over surface 16 are spaced so that the distance between adjacent steps is less than the diameter of an ultrasound beam generated by transducer 20. Accordingly, there will be an overlap of information obtained from adjacent datapoints. A typical spacing between adjacent datapoints utilizing the above-described transducer at a distance of about ½ inch above a surface of mass 10 is about 0.02 inches.

Transducer 20 detects echoes at the respective positions defined over surface 16, and relays information about the detected echoes to receiver 35. Receiver 35 digitizes the information and sends it to processor 34. Processor 34 associates digitized signals received from receiver 35 with relative positions of transducer 20 over surface 16, and analyzes the signals. Specifically, at least one physical attribute of the signals is processed by processor 34. Processor 34 can comprise a commercially or otherwise available software package, such as, for example, Panametrics™, Inc. Multiscan™ software. A physical attribute that will typically be analyzed is an amplitude of the echo signal, but other physical attributes, such as, for example, a phase of the signal can be analyzed in addition to, or instead of, the amplitude. If a magnitude of the analyzed physical attribute is below a threshold value, the data pertaining to the echo can be rejected from further consideration and processing. For instance, if the threshold is based on an amplitude of the detected signal, the signals having amplitudes below the threshold can be rejected from further consideration by processor 34. It is noted that if more than one physical attribute is considered by processor 34, the threshold can be based on any one of the physical attributes, or in other embodiments, on more than one of the physical attributes. For instance, if both phase and amplitude are to be considered by processor 34, then the data can be first sorted based on amplitude, and then all data having sufficient amplitude can be retained and processed relative to phase.

In particular applications, the threshold utilized for sorting data is based on an amplitude of the data. The data found to have sufficient amplitude is subsequently grouped into clusters, with the clusters being defined as echoes from adjacent positions of the plurality of tested positions. Clusters of data are assumed to arise from a common defect (the assumption is found to be acceptable, even though it is recognized that clusters of data can also result from several small, separate defects that are too close together to be resolved by methodology applied in particular applications). Accordingly, the separate echoes associated with a common cluster are analyzed and considered together to generate information about a defect in the target material 10. Such analysis can include calculation of a depth and integrated amplitude for each cluster. The integrated amplitude is defined as the sum of the amplitudes of the separate datapoints in the cluster, multiplied by the area represented by a single datapoint. The area represented by a single datapoint equals the product of distances between scan points in the X and Y raster directions. It is found that the assumption that each data cluster pertains to a single defect is generally valid in that the probability that any two data clusters will overlap is small for the high purity materials typically utilized as sputtering target materials.

Figure 3:
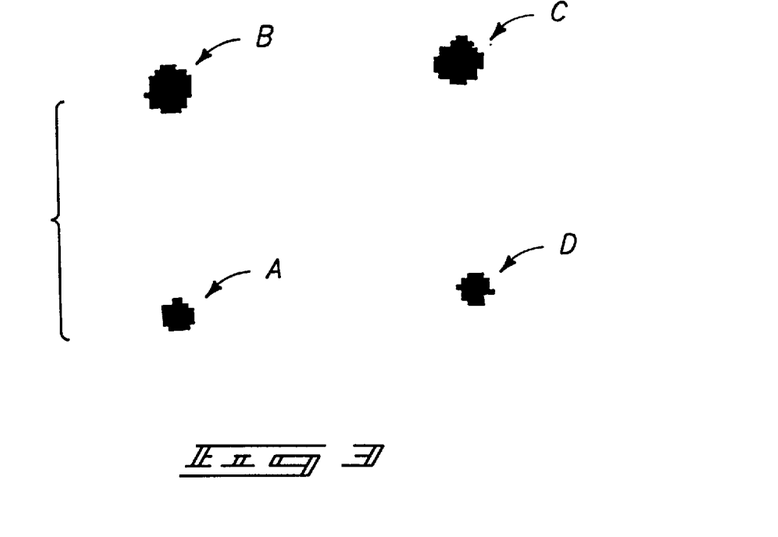
FIG. 3 is a view of the FIG. 1 image after processing in accordance with the present invention.

FIG. 3 shows the data of FIG. 1 enhanced utilizing methodology of the present invention. Specifically, all datapoints having an amplitude above a threshold value have been determined, and subsequently clusters have been defined to comprise adjacent datapoints with above-threshold amplitudes. The clusters correspond to the data of locations "A", "B", "C", and "D". The datapoints retained in the clusters have been scaled to the same amplitude as one another (i.e., are shown at the same level of gray-scale as one another), and now provide information about the shape of the defects which generated the clusters. Note that cluster "C" is larger than cluster "A" in FIG. 3, even though if clusters "C" and "A" were compared to one another from the prior art methodology of FIG. 1, and were compared solely on the basis of the highest amplitude datapoint of clusters "C" and "A" in FIG. 1 (with increasing amplitudes in FIG. 1 being reflected by increasing gray-scale), clusters "C" and "A" would have been determined to be the same size as one another.

FIGS. 1 and 3 show amplitude information being conveyed as a relative level of grayscale. It is noted, however, that other plotting methods can be utilized in applications of the present invention for conveying information about the respective magnitudes of measured data from different datapoints. For instance, the magnitudes of measured data can be grouped into two or more levels, and different colors can be assigned to the different levels.

In particular aspects of the present invention, a mathematical model is created and utilized to assist in interpreting the integrated amplitude data described above. Initially, a reference target material is formed having flat bottom holes of various diameters and depths provided therein. A C-scan in accordance with the procedures described above relative to FIG. 2 is then conducted on the reference, and the mathematical model is generated to correlate flat bottom hole diameter and depth to an integrated amplitude of data clusters detected from the flat bottom holes. The model preferably uses an equation that reflects the geometry and intensity of the ultrasonic beam. An integrated amplitude of a cluster from the test sample can then be compared to the model and correlated with the information generated from the model. The integrated amplitudes of the clusters of the test sample can be expressed as "$FBH_{eq}$", which is a flat bottom hole equivalent, and which quantitates the cluster integrated amplitude in terms of a flat bottom hole that would produce equal integrated amplitude if located at the same depth as the defect in a sample.

The present invention can be utilized to determine $FBH_{eq}$ for all defects within a tested region of a sample, rather than simply counting the number of defects larger than a specified equivalent FBH, or within a specified FBH range, as would be practiced by conventional methods. Methods of the present invention can also compensate for non-linear relationships between integrated amplitude and flat bottom hole diameter, as well as interactions between integrated amplitude and depth. As a result, methods of the present invention can improve the accuracy and precision of defect size measurements relative to prior art methods, and can do so over a broader range of size and depth. An exemplary mathematical model utilized in methodology of the present invention is:

$$FBH_{eq}=(a_1+b_1*depth+c_1*depth^2)+(a_2+b_2*depth+c_2*depth^2)*(integrated\ amplitude)^x$$

wherein $a_1$, $a_2$, $b_1$, $b_2$, $c_1$, $c_2$ and x are constants determined by fitting to measured C-scan data of flat bottom holes.

Figure 4:
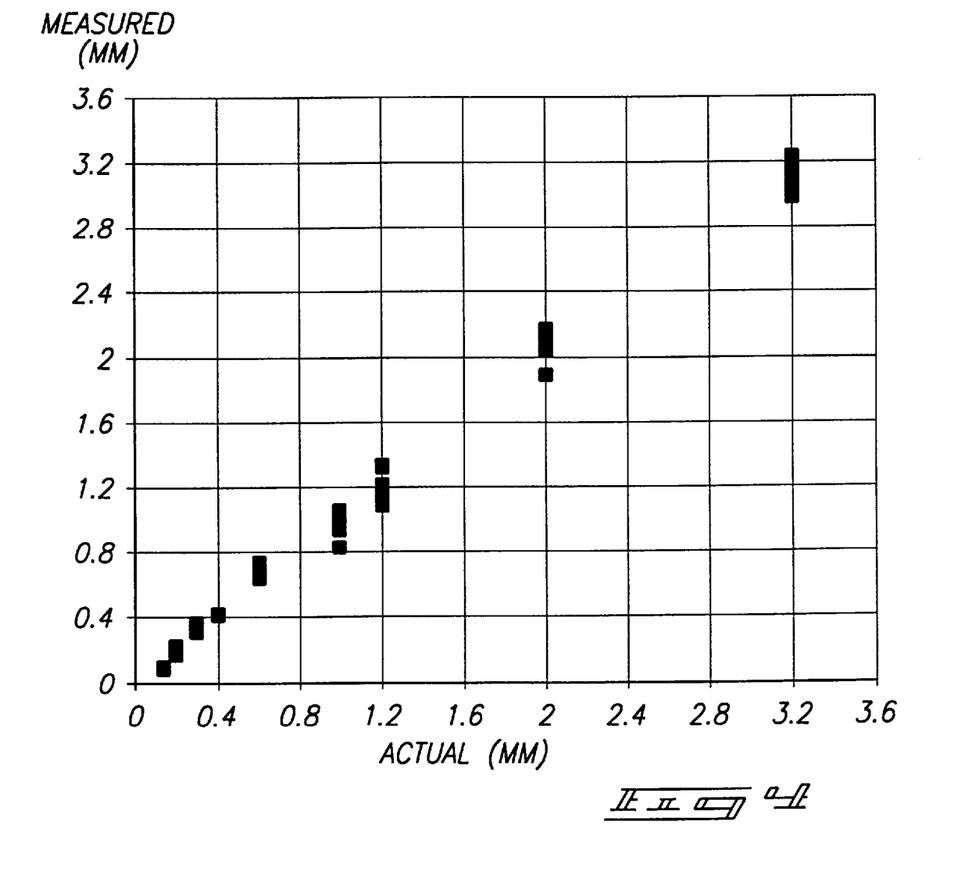
FIG. 4 is a graph of flat bottom hole diameter calculated utilizing methodology of the present invention versus actual flat bottom hole diameters.

A typical flat bottom hole reference standard utilized in methodology of the present invention is made from a sputter target material similar to the sample which is to be tested, and covers ranges of defect depth and size which are to be measured (for example, from 0.125 inches to 0.75 inches depth, and from 0.15 to 3.2 millimeter diameters). The fit of model constants is determined by minimizing the residual square of the difference between the actual flat bottom hole diameter and the $FBH_{eq}$ calculated from C-scan data. The residual is summed over various flat bottom hole sizes and depths, and, in some applications, over multiple scans of multiple flat bottom hole standards. The utilization of multiple scans can provide more accurate determination of fit parameters than is achieved by calculating the parameters from single scans. Knowledge of the residual can allow the performance of an ultrasonic testing system to be closely monitored, and can enable differences between transducers and instruments to be quantified. A model fit can be illustrated by plotting measured $FBH_{eq}$ versus actual flat bottom hole diameter, and an exemplary fit is shown in the graph of FIG. 4. Such graph shows that a model of the present invention can be effective over a wide range of depths and flat bottom hole sizes.

Figure 5:
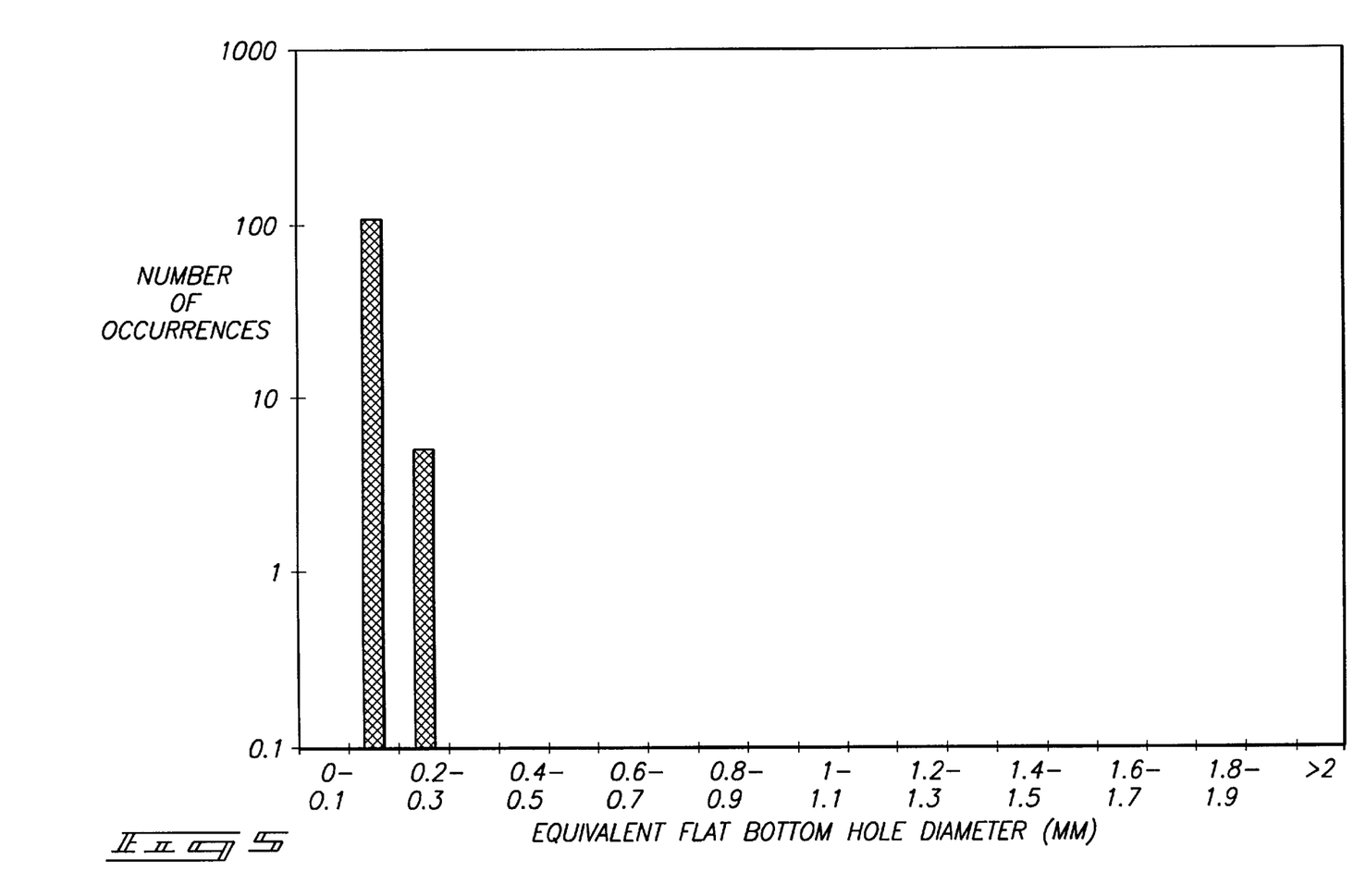
FIG. 5 is a histogram graph showing defects in a material, with such histogram indicating the number of occurrences of defects corresponding to particular ranges of equivalent flat bottom hole diameters.

One way of presenting $FBH_{eq}$ results is to display the results in the form of a histogram showing the number of defects per size interval. FIG. 5 illustrates an exemplary histogram. Such histogram can provide a visual method for communicating the numbers and sizes of defects in a material.

Another way of presenting $FBH_{eq}$ results is to calculate a single figure-of-merit from the $FBH_{eq}$ datasets associated with a target material. The figure-of-merit can be calculated as a constant times the sum of $(FBH_{eq})^2$ (or the sum of $(FBH_{eq})$ raised to any power), divided by the volume of material analyzed. The constant can be any number, and in an exemplary application is 600. A figure-of-merit determination can be useful in rejecting targets having larger sizes of defects. Generally, when defect size increases, the probability of causing sputtering problems during deposition of thin films also increases. The figure-of-merit can provide a single number for indicating the likelihood that defects in a sample will lead to problems during sputtering, and can therefore provide a material acceptance criteria during processing of sputtering targets. The figure-of-merit analysis can be particularly useful for process improvement purposes.

Figure 6:
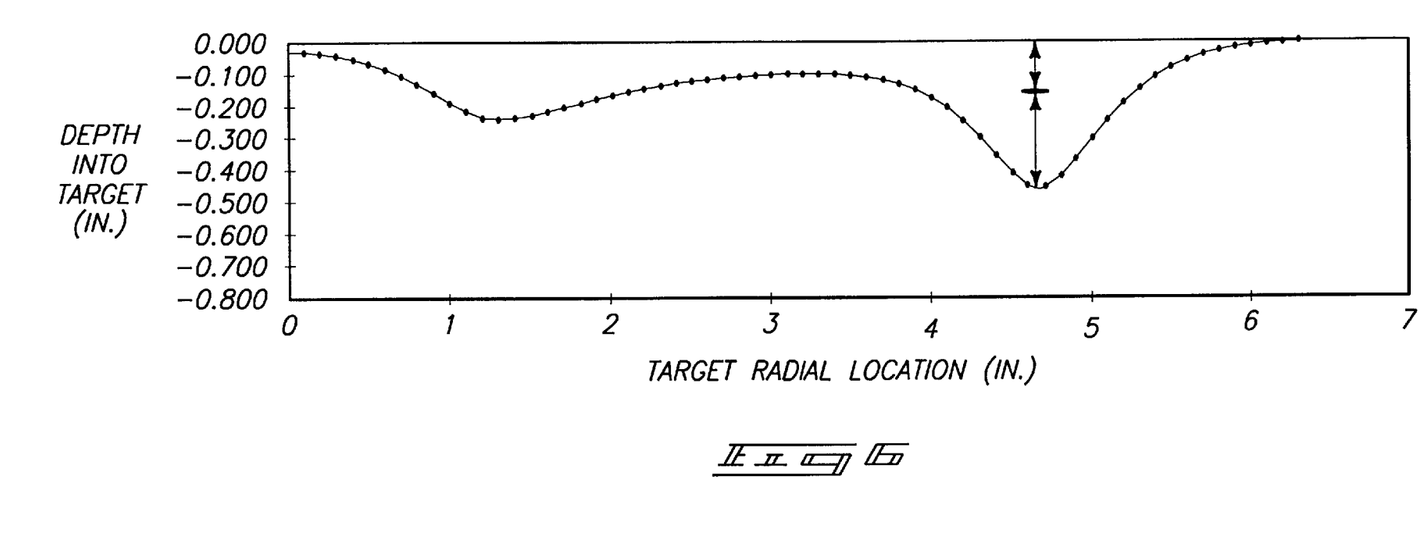
FIG. 6 is a graph of a target erosion profile showing the depth of the target erosion plotted against a radial location along the target.
Figure 7:
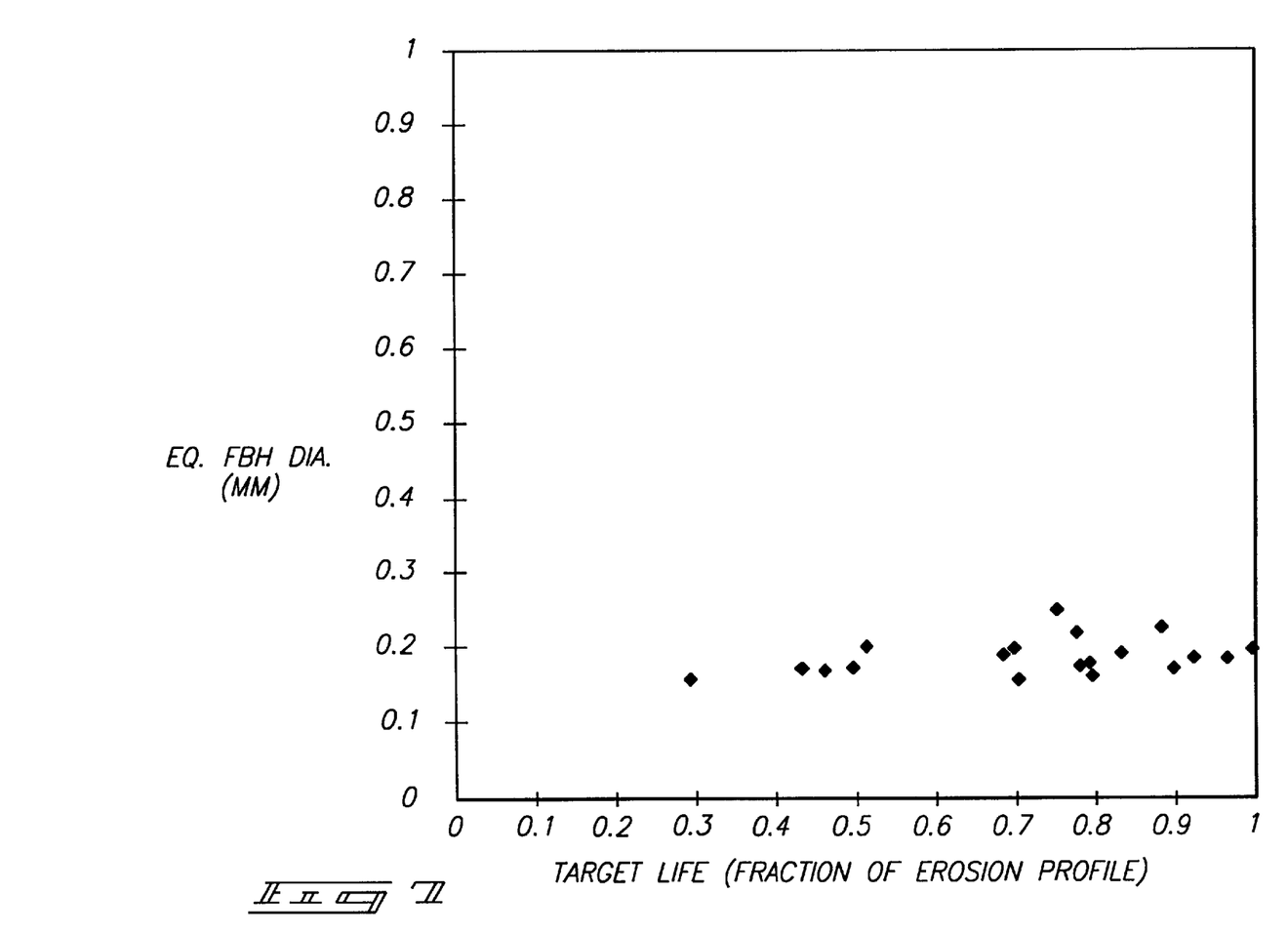
FIG. 7 is a graph of flat bottom hole equivalents (in millimeters) versus target life (as a fraction of an erosion profile).

Among the advantages of the present invention is that the invention can enable relatively precise determination of defect location within a target material. The sizes and numbers of defects can then be plotted relative to depth, radius, x-coordinate, and/or y-coordinate within a sample. In a particular embodiment, the defect location can be compared to a complexly shaped volume of material expected to be consumed from a sputter target. Such can be accomplished by measuring the profile of sputter targets previously subjected to erosion in a sputtering apparatus to determine relative material erosion rate as a function of radial position (an exemplary profile is shown in FIG. 6). The figure of merit and/or histogram can then be calculated for the convoluted volume of material that will be expected to be sputtered from a target (with the predicted erosion profile being determined by, for example, predicting the profile to be identical to erosion profiles determined for previously sputtered targets that had been sputtered in a similar apparatus to that which the sample target is to be utilized in). By analyzing only the sputterable volume of material, the results can correlate more directly to the target sputter performance. From the predicted erosion profile, the point in the target lifetime can be calculated at which each defect is expected to be exposed during sputtering. Such information can be presented as a scatter plot of exposed defect size versus target lifetime, as shown in FIG. 7. An additional benefit that can be obtained by utilizing a predicted erosion profile is that the amount of data processed for a particular target can be reduced. Specifically, in one aspect of the invention it is recognized that the inhomogeneities in the material of the target that will be sputtered (i.e., that is within the sputtered portion of the erosion profile) are likely more problematic than in inhomogeneities at other locations of the target material. Accordingly, only data obtained at positions of the target which will be sputtered is analyzed and evaluated for inhomogeneities.

Referring again to FIG. 2, an echo 24 is shown generated by an inhomogeneity present within material 10. A plurality of inhomogeneities 40 and 42 are shown within material 10, with inhomogeneities 40 corresponding to voids and inhomogeneities 42 corresponding to inclusions of solid material. Note that the voids are stretched within material 10 to extend substantially parallel relative to upper surface 16. Such is common for voids formed in sputtering targets, as described in, for example, U.S. Pat. No. 5,887,481. In practice, an ultrasonic beam emanating from transducer 20 is typically broad enough so that only some of the beam is reflected back from a particular defect, and other portions of the beam pass through or around the defect. Such other portions can then be reflected back by other defects, by the back surface 18 of material 10, or can pass entirely through material 10. In particular applications of the present invention, the portions of the beam reflected back from surface 18 are recorded by transducer 20 and utilized by processor 34 during analysis for defects in material 10. Such applications can be easiest to utilize if surface 18 is smooth and parallel to surface 16. Note that echoes bouncing back to transducer 20 from backside 18 can have portions deflected, absorbed, scattered, etc., by defects within material 10, as well as having portions which pass around the defects to transducer 20. Accordingly, echoes from backside 18 can carry information about defects in material 10 which can provide additional detection/characterization capability, or can enhance understanding of the defects when utilized alone or in combination with information obtained from direct reflection of ultrasonic information from the defects to transducer 20.

Figure 8:
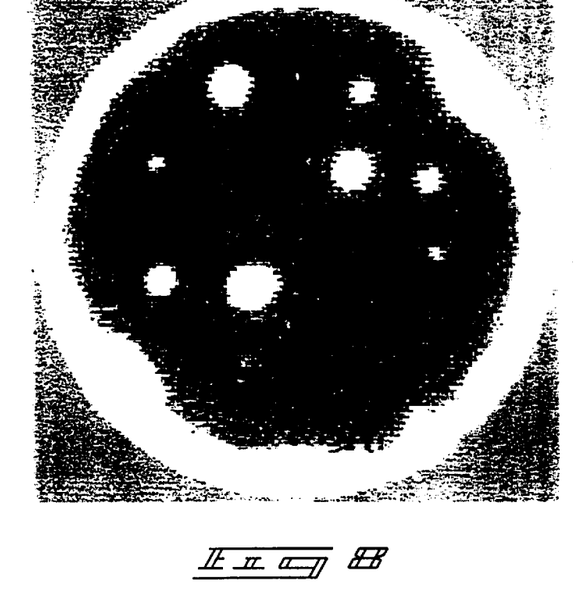
FIG. 8 is an ultrasonic echo shadow of a target, with the echo shadow being produced in accordance with methodology of the present invention.

In particular aspects of the invention, it is recognized that absorption and scattering of sound is expected to be different for solid inclusions relative to other types of defects in materials having sputtering target forms. Defects without solid inclusions tend to be voids, clusters of voids, or small cracks that are flattened parallel to a target surface by mechanical deformation processing steps utilized to form microscopic characteristics within sputtering targets. Such defects are expected to exhibit different shape and sound reflections/scattering/absorbance properties than defects with rigid, solid inclusions. Accordingly, the additional scattering and absorption information provided by a back surface echo can enable defects in target materials to be discriminated amongst a group that contains solid inclusions and a group which does not. FIG. 8 illustrates an echo pattern obtained from echoes generated by a transducer over the frontside of a target material, using ultrasound reflected off of the backside of the target material, and detected by the transducer over the frontside of the target material. The image illustrates that the echo pattern contains significant information about defects within the material. This information can be obtained using similar techniques as are used to obtain information from typical reflection-mode C-scan data.

Transducer 20 has a surface 50 from which ultrasonic radiation is projected and received. In the shown embodiment, surface 50 is substantially parallel with surface 16 of material 10. Such is a typical orientation of transducer 20 relative to upper surface 16. However, it is noted that the invention also encompasses applications wherein transducer 20 is tilted, such that surface 50 extends at angle Θ relative to upper surface 16. Such tilted orientation of transducer 20 is shown in dashed-line view in FIG. 2. Angle Θ can be, for example, greater than 5° and less than 90°, and in particular embodiments can be from about 10° to about 30°. An advantage of tilting surface 50 of transducer 20 relative to upper surface 16 is that such can enable inhomogeneities 40 and 42 to be distinguished by type. Specifically, it is noted that the void or gas-filled regions in mechanically processed samples (designated as inhomogeneities 40 in FIG. 2) tend to be flattened and stretched approximately parallel to upper surface 16. In contrast, solid inclusion regions 14 tend to be substantially 3-dimensional. Accordingly, if transducer 20 is tilted there will be lesser or no change in reflected signal from inclusion regions 42 relative to the signal received from a non-tilted transducer, but the reflected signal from void regions 40 will show a greater decrease in amplitude.

Figure 9:
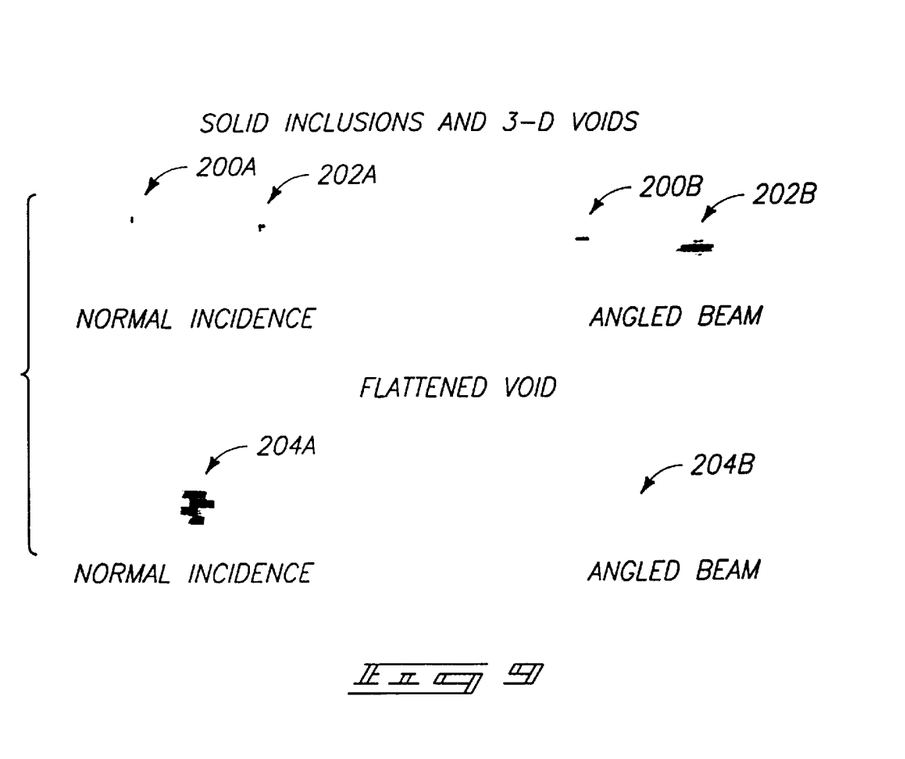
FIG. 9 illustrates the magnitude and position of sonic echo amplitudes received from various defects utilizing either normal incidence ultrasound or angled beam ultrasound.

FIG. 9 shows a comparison of echo data obtained with normal incidence and angled beam incidence for three dimensional structures (three-dimensional voids or inclusions) relative to flattened voids. A top panel of FIG. 9 compares amplitudes of echoes (200*a* and 200*b*) obtained from a first solid inclusion utilizing normal incidence 200*a* and angled beam incidence 200*b* (with the beam being angled at about 15° relative to normal). The top panel of FIG. 9 also compares amplitudes of echoes (202*a* and 202*b*) obtained from a second inclusion utilizing normal incidence 202*a*, and the angled beam incidence 202*b*. The lower portion of FIG. 9 compares amplitudes of echoes (204*a* and 204*b*) obtained from a flattened void (i.e. a void such as, for example, void 40 of FIG. 2 which is stretched in one or more directions substantially parallel to upper surface 16 of the FIG. 2 target material) obtained using a transducer with normal incidence 204*a*, and angled beam incidence 204*b*. It is noted that there is no detection of a signal above threshold when utilizing the angled beam incidence on the flattened void. It is also noted that the uneven appearance of image 204A is caused by a small amount of variation in the X-coordinate location of the raster scan between adjacent rows of the scans. This variation can be controlled by typical C-scan operation methods if it becomes large enough to affect data clustering.

Figure 10:
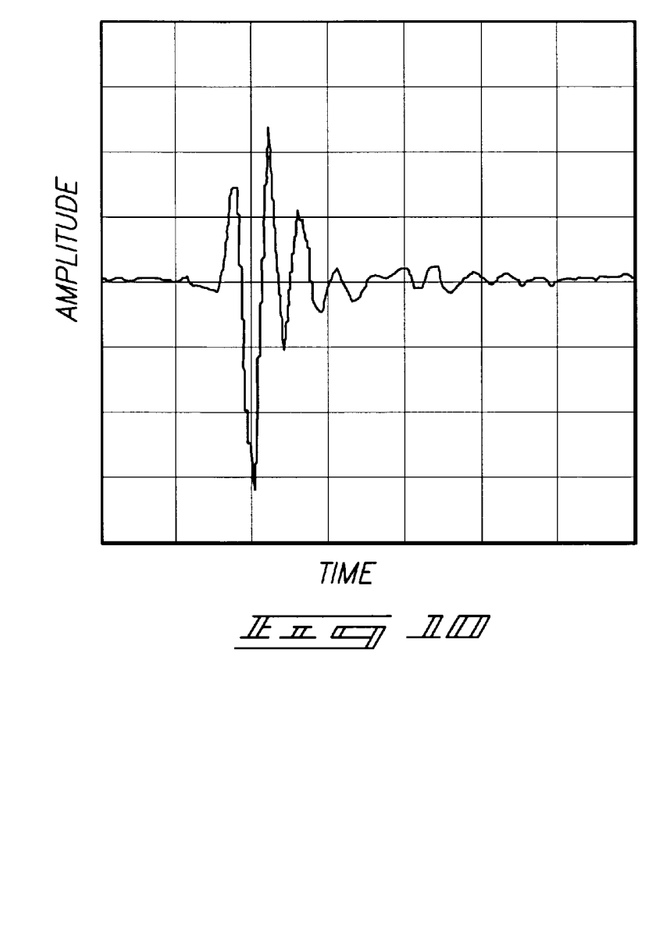
FIGS. 10 and 11 illustrate ultrasound echoes received from defects in a material, and specifically indicate echoes received from a void-type defect and a solid-inclusion-type defect, respectively.
Figure 11:
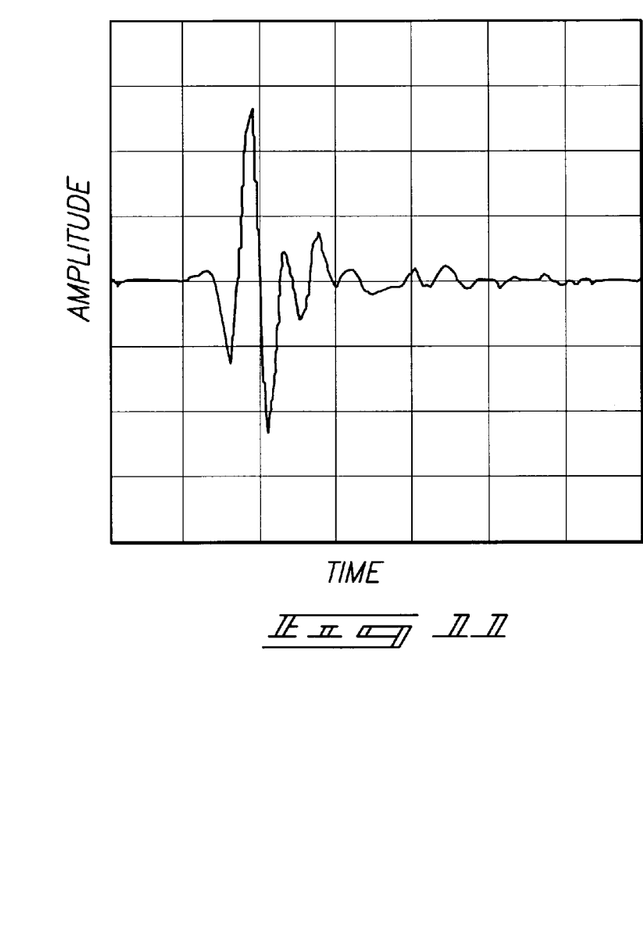

Another method of the present invention which can be utilized for discriminating between solid inclusions and other defects in sputter materials is described with reference to FIGS. 10 and 11. Such method utilizes phase information from returned ultrasonic pulses. It is found that a pulse returned from a solid inclusion of higher acoustic impedance (relative to the material) is typically reversed in phase relative to that returned from a defect of lower acoustic impedance (relative to the material). This can enable discrimination of ultrasonic signals returned from lower acoustic impedance defects (such as, for example, voids, entrapped gases, and flat bottom holes) from signals returned from higher acoustic impedance defects (such as, for example, various solid inclusions). Phase analysis of the echoes can be accomplished by manual analysis of signals from specific defects, or by automated signal processing techniques utilizing, for example, processor 34 of FIG. 2. FIGS. 10 and 11 show the phase reversal between a signal reflected from a flat bottom hole (FIG. 10) and a solid inclusion (FIG. 11). The automated analysis can allow identification of all defects by type (void or solid inclusion), and can even allow use of a model based on solid inclusions to calculate the size of the defects identified as solid inclusions.

Figure 12:
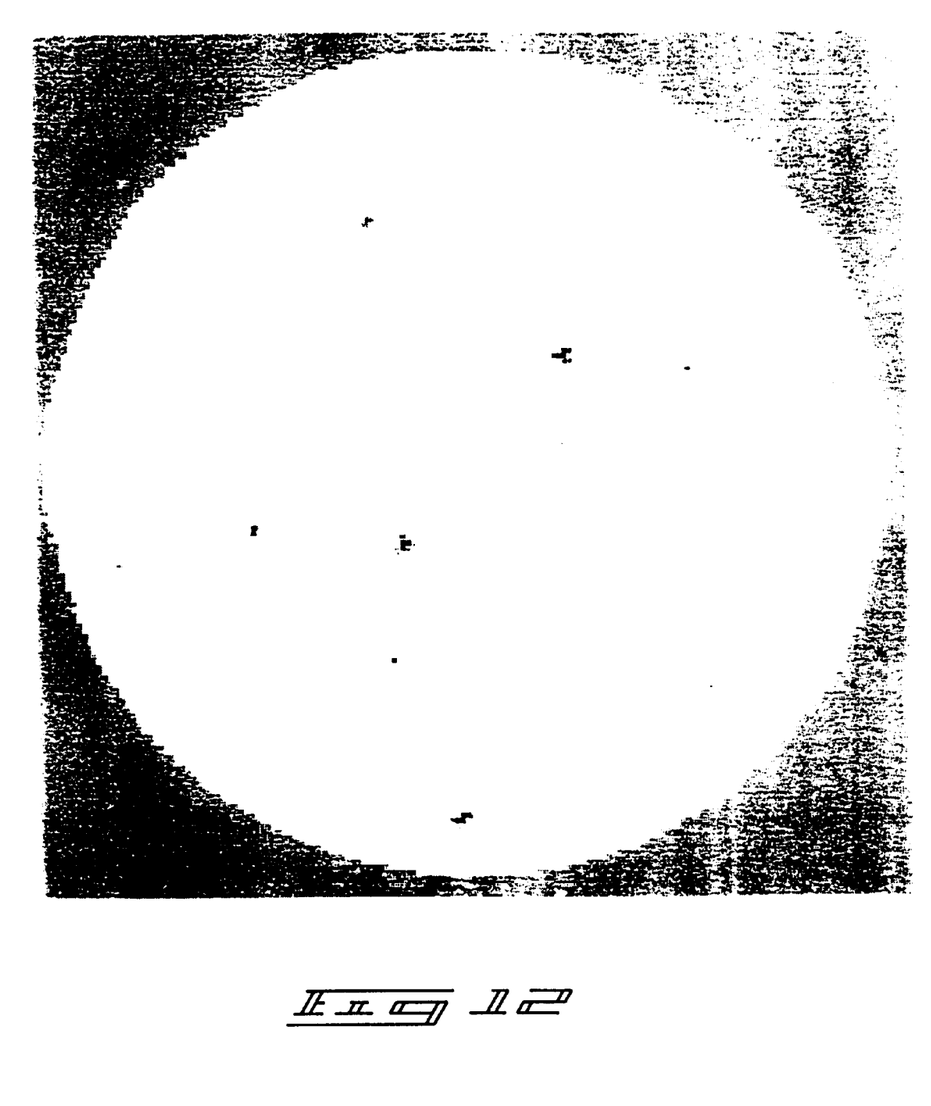
FIG. 12 is a view of an image of a solid inclusion reference standard obtained in accordance with methodology of the present invention.

In embodiments of the present invention in which ultrasonic testing is utilized for detecting solid inclusions, a solid inclusion reference standard can be formed. A reference standard can be formed by providing inclusions of various sizes at various depths within a material so that a model can be developed relating ultrasonic indications to the size and depth of a solid inclusion. The inclusions can be, for example, spherical, and the material of the reference standard is preferably similar to the material which is to be inspected. The use of a solid inclusion reference standard can enable assessment of ultrasonic testing performance for detection and measurement of solid inclusions in sputter target materials. An exemplary reference standard comprises an aluminum matrix with sapphire ($Al_2O_3$) inclusions. Such standard can be created via powder metallurgy, or also via thermomechanical means (e.g., diffusion bonding). In particular applications, a solid aluminum disk reference standard is made with 4.75, 2.36, 1.0, and 0.4 mm diameter sapphire spheres located at 0.3, 0.5, and 0.7 inches depth. A C-scan image of an aluminum reference standard having sapphire inclusions provided therein is shown in FIG. 12.

It is noted that the flat-bottom-hole equivalent ($FBH_{eq}$) described above is an exemplary defect equivalent that can be utilized in methods of the present invention, and that other defect equivalents could be utilized in methodology of the present invention. For instance, the inclusions formed in the reference standard of FIG. 12 could be utilized to generate a model similar to that described for determining flat-bottom-hole equivalents, but which would instead determine sapphire-sphere-inclusion equivalents. In other words, flat bottom holes are one type of reference defect that can be utilized in methods of the present invention, and other reference defects, such as, for example, sapphire spheres, can also be utilized in methods of the present invention.

Although the invention is described herein for methods of utilizing ultrasonic evaluation of materials, it is to be understood that various aspects of the invention can be utilized with other evaluation methods. For instance, the data analysis procedures can be utilized with other methods in which a sample material and reference are exposed to a common examination method, and wherein results obtained from the sample are compared with results obtained from the reference. The term "common examination method" refers to a method which is the same in technique, but not necessarily the same in time or apparatus.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method for testing substantially homogeneous materials for inhomogeneities, comprising:
   defining a plurality of positions across at least a portion of a material;
   sequentially irradiating at each of the positions of said plurality of positions with sonic energy;
   detecting individual echoes induced by said sonic energy at each sequentially irradiated position and associating at least some of the detected echoes with individual positions of the plurality of positions that triggered the at least some of the detected echoes;

processing information pertaining to a measurement of at least one physical attribute of the at least some of the detected individual echoes to sort the at least some of the detected individual echoes into a first group indicative of inhomogeneities in the material, and a second group which does not indicate inhomogeneities in the material;

sorting the individual echoes of the first group into clusters, with the clusters being defined as echoes from adjacent positions of the plurality of positions;

analyzing and considering together the individual echoes associated with a common cluster to generate information about an inhomogeneity in the material; and comparing the generated information with data obtained from a reference material.

2. The method of claim 1 further comprising printing the generated information as a plot of magnitude of the measured physical attribute versus position in the material.

3. The method of claim 1 wherein the at least one measured physical attribute includes an amplitude of the detected individual echoes; and wherein the analyzing and considering together the individual echoes associated with the common cluster comprise determining an integrated amplitude of the cluster.

4. The method of claim 1 wherein the material is in the form of a billet which is to be utilized in forming a sputtering target, and which does not yet have the grain size of the sputtering target that is to be formed from the billet.

5. The method of claim 1 wherein the material is in the form of a sputtering target.

6. The method of claim 1 wherein the at least one physical attribute comprises an amplitude of the detected individual echoes.

7. The method of claim 1 wherein the at least one physical attribute comprises an amplitude of the echoes and further comprising:

forming an integrated amplitude of the echoes associated with the common cluster;

wherein the comparing the generated information to data obtained from a reference sample comprises comparing the integrated amplitude with data obtained from the reference sample, the reference sample having reference inhomogeneities therein to obtain a reference inhomogeneity equivalent of the integrated amplitude.

8. The method of claim 7 wherein the reference inhomogeneities are sapphire spheres.

9. The method of claim 7 wherein the reference inhomogeneities are flat bottom holes.

10. The method of claim 7 further comprising displaying a plurality of the reference inhomogeneity equivalents as a histogram.

11. The method of claim 1 wherein the material is in a shape and form of a sputtering target and wherein the at least one physical attribute comprises an amplitude of the echoes, and further comprising:

forming an integrated amplitude of the echoes associated with the common cluster, determining a size and depth of inhomogeneities from comparison of the integrated amplitudes with a reference standard;

determining an erosion profile of the sputtering target; and wherein only the sputtering target material within the erosion profile is evaluated to determine size and depth of inhomogeneities therein.

12. The method of claim 1 wherein the material is in a shape and form of a sputtering target, and wherein the at least one physical attribute comprises an amplitude of the echoes, and further comprising:

forming an integrated amplitude of the echoes associated with the common cluster;

determining a size and depth of inhomogeneities from comparison of the integrated amplitudes with a reference standard;

determining an erosion profile of the sputtering target; and calculating the point in target lifetime at which one or more of the inhomogeneities will be exposed during sputtering.

13. The method of claim 1 wherein the at least one physical attribute comprises an amplitude of the detected individual echoes, wherein a plurality of clusters are identified, and further comprising:

forming a plurality of integrated amplitudes, each of the integrated amplitudes being formed from the echoes associated with a different common cluster than the others of the integrated amplitudes;

comparing the integrated amplitudes with data obtained from a reference sample having flat-bottomed holes therein to obtain a flat bottom hole equivalent for each of the integrated amplitudes, and to thus obtain a plurality of flat bottom hole equivalents; and converting the plurality of flat bottom hole equivalents into a single figure-of-merit.

14. The method of claim 13 wherein a plurality of materials are tested, a separate figure-of-merit is generated for each material, and the materials are sorted relative to one another based on the figure-of-merits.

15. The method of claim 1 wherein the at least one physical attribute comprises a phase of the detected individual echoes.

16. The method of claim 1 wherein the at least one physical attribute comprises a phase of the echoes, and wherein the information generated about the inhomogeneity includes a determination of whether the inhomogeneity comprises a solid inclusion.

17. The method of claim 1 wherein the sonic energy has a frequency of from 10 MHz to 100 MHz.

18. The method of claim 1 wherein the sonic energy has a frequency of from 5 MHz to 25 MHz.

19. The method of claim 1 wherein a common transducer is utilized for the irradiating and the detecting of echoes.

20. The method of claim 1 wherein the material comprises a frontside and an opposing backside, wherein the irradiating is from a transducer in a direction through the frontside and toward the backside, and wherein the detected echoes include echoes deflected from the inhomogeneity back toward the transducer, as well as echoes deflected from the backside back toward the transducer.

21. The method of claim 1 wherein the material comprises a frontside surface, wherein the irradiating is from a transducer having a transducer surface directly over the frontside surface, and wherein the transducer surface is substantially parallel to the frontside surface.

22. The method of claim 1 wherein the material comprises a frontside surface, wherein the irradiating is from a transducer having a transducer surface directly over the frontside surface, and wherein the transducer surface is not substantially parallel to the frontside surface.

23. The method of claim 1 wherein the material consists essentially of metal.

24. The method of claim 1 wherein the material comprises one or more of aluminum, copper, silicon, titanium, tungsten, tantalum and gold.

25. The method of claim 1 wherein the material consists essentially of one or more of aluminum, copper, titanium, and silicon.

26. A method for testing a plurality of sputtering targets, comprising:
for each target of the plurality of targets:
defining a plurality of positions across at least a portion of the sputtering target;
sequentially irradiating at each of the positions of said plurality of positions with sonic energy, and sequentially detecting amplitudes of individual echoes induced by said sonic energy;
processing the amplitudes to sort the individual echoes into a first group indicative of inhomogeneities in the sputtering target, and a second group which does not indicate inhomogeneities in the sputtering target;
sorting the individual echoes of the first group into clusters, with the clusters being defined as individual echoes from adjacent positions of the plurality of positions;
generating an integrated amplitude for the individual echoes associated with a common cluster; and
calculating a figure-of-merit for the sputtering target from the integrated amplitudes associated with the sputtering target; and
sorting the plurality of sputtering targets based on the respective figure-of-merits of the sputtering targets.

27. The method of claim 26 further comprising detecting a phase of the echoes.

28. The method of claim 26 further comprising detecting a phase of the echoes, and utilizing the phase to determine whether at least one of the detected inhomogeneities comprises a solid inclusion.

29. The method of claim 26 wherein the sonic energy has a frequency of from 10 MHz to 100 MHz.

30. The method of claim 26 wherein the sonic energy has a frequency of from 5 MHz to 25 MHz.

31. The method of claim 26 wherein each of the targets comprises a frontside surface, wherein the irradiating is from a transducer having a transducer surface directly over the frontside surface, and wherein the transducer surface is substantially parallel to the frontside surface.

32. The method of claim 26 wherein each of the targets comprises a frontside surface, wherein the irradiating is from a transducer having a transducer surface directly over the frontside surface, and wherein the transducer surface is not substantially parallel to the frontside surface.

33. The method of claim 26 wherein each of the targets consists essentially of metal.

34. The method of claim 26 wherein each of the targets comprises one or more of aluminum, copper, silicon, titanium, tungsten, tantalum and gold.

35. The method of claim 26 wherein each of the targets consists essentially of one or more of aluminum, copper, titanium, and silicon.

36. A method for testing a material having a form and shape of a sputtering target, comprising:
checking the material for size and location of inhomogeneities within the material by:
determining an erosion profile for the sputtering target;
defining a plurality of positions across at least a portion of the material;
sequentially irradiating at each of the positions of said plurality of positions with sonic energy, and sequentially detecting amplitudes of echoes induced by said sonic energy; and
for only the material within the erosion profile:
processing the amplitudes to sort the echoes into a first group indicative of inhomogeneities in the material, and a second group which does not indicate inhomogeneities in the material;
sorting the echoes of the first group into clusters, with the clusters being defined as echoes from adjacent positions of the plurality of positions;
generating an integrated amplitude for the echoes associated with a common cluster; and
comparing the integrated amplitudes with reference inhomogeneities to estimate the size of the inhomogeneities and depth of the inhomogeneities within the material.

37. A method for testing a material having a form and shape of a sputtering target, comprising:
checking the material for size and location of inhomogeneities within the material by:
defining a plurality of positions across at least a portion of the material;
sequentially irradiating at each of the positions of said plurality of positions with sonic energy, and sequentially detecting amplitudes of echoes induced by said sonic energy;
processing the amplitudes to sort the echoes into a first group indicative of inhomogeneities in the material, and a second group which does not indicate inhomogeneities in the material;
sorting the echoes of the first group into clusters, with the clusters being defined as echoes from adjacent positions of the plurality of positions;
generating an integrated amplitude for the echoes associated with a common cluster; and
comparing the integrated amplitudes with reference inhomogeneities to estimate the size of the inhomogeneities and depth of the inhomogeneities within the material;
determining an erosion profile for the sputtering target; and
for at least one of the inhomogeneities, estimating the point during target lifetime at which said at least one inhomogeneity will be exposed.

38. The method of claim 37 wherein only material within the erosion profile is evaluated by generating the integrated amplitudes and comparing the integrated amplitudes with the reference inhomogeneities.

39. The method of claim 37 further comprising detecting a phase of the echoes.

40. The method of claim 37 further comprising detecting a phase of the echoes, and utilizing the phase to determine whether at least one detected inhomogeneity comprises a solid inclusion.

41. The method of claim 37 wherein the sonic energy has a frequency of from 10 MHz to 100 MHz.

42. The method of claim 37 wherein the sonic energy has a frequency of from 5 MHz to 25 MHz.

43. The method of claim 37 wherein the target comprises a frontside surface, wherein the irradiating is from a transducer having a transducer surface directly over the frontside surface, and wherein the transducer surface is substantially parallel to the frontside surface.

44. The method of claim 37 wherein the target comprises a frontside surface, wherein the irradiating is from a transducer having a transducer surface directly over the frontside surface, and wherein the transducer surface is not substantially parallel to the frontside surface.

45. The method of claim 37 wherein the target consists essentially of metal.

46. The method of claim 37 wherein the target comprises one or more of aluminum, copper, antimony, silver, titanium, tungsten, tantalum and gold.

47. The method of claim 37 wherein the target consists essentially of one or more of aluminum, copper, titanium, antimony and silver.

* * * * *

UNITED STATES PATENT AND TRADEMARK OFFICE
CERTIFICATE OF CORRECTION

PATENT NO. : 6,439,054 B1
DATED : August 27, 2002
INVENTOR(S) : Russell B. Gore et al.

It is certified that error appears in the above-identified patent and that said Letters Patent is hereby corrected as shown below:

Column 2,
Line 27, replace "findamental" with -- fundamental --.

Column 5,
Line 15, replace "with" with -- which --.

Signed and Sealed this

Fourth Day of March, 2003

JAMES E. ROGAN
*Director of the United States Patent and Trademark Office*